(12) United States Patent
Neal

(10) Patent No.: US 6,649,129 B1
(45) Date of Patent: *Nov. 18, 2003

(54) METHOD AND APPARATUS FOR CONCENTRATING A VOC SAMPLE

(75) Inventor: David M. Neal, Hamilton, OH (US)

(73) Assignee: Teledyne Tekmar Company, Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/868,875

(22) Filed: Jun. 4, 1997

Related U.S. Application Data

(63) Continuation of application No. 08/556,620, filed on Nov. 13, 1995, now abandoned, and a continuation of application No. 08/556,666, filed on Nov. 13, 1999, now Pat. No. 5,691,487, and a continuation of application No. 08/556,661, filed on Nov. 13, 1995, now Pat. No. 5,689,073.

(51) Int. Cl.[7] .......................... G01N 30/06; G01N 30/38
(52) U.S. Cl. .......................... 422/89; 422/88; 73/23.35; 73/23.41; 73/23.42; 96/102; 96/103; 436/161; 436/177; 436/178
(58) Field of Search .................. 422/88, 89; 436/161, 436/177, 178; 73/23.35, 23.41, 23.42; 96/102, 103

(56) References Cited

U.S. PATENT DOCUMENTS

| | | | |
|---|---|---|---|
| 4,600,559 A | 7/1986 | Hiatt | 422/89 |
| 4,872,334 A | 10/1989 | Watanabe | 73/23.1 |
| 4,962,042 A | 10/1990 | Morabito et al. | 436/161 |
| 5,001,071 A | 3/1991 | Morabito et al. | 436/161 |
| 5,108,705 A | 4/1992 | Rounbehler et al. | 422/89 |
| 5,152,176 A | 10/1992 | Bryselbout et al. | 73/23.41 |
| 5,166,076 A | 11/1992 | Muller et al. | 436/161 |
| 5,240,604 A * | 8/1993 | Cortes et al. | |
| 5,268,302 A | 12/1993 | Rounbehler et al. | 436/96 |
| 5,338,514 A | 8/1994 | Morabito et al. | 422/89 |
| 5,392,634 A | 2/1995 | Asano et al. | 73/23.42 |
| 5,411,707 A | 5/1995 | Hiatt | 422/68.1 |
| 5,447,556 A * | 9/1995 | Pleil et al. | 96/102 |
| 5,467,635 A | 11/1995 | Nakagawa et al. | 73/23.35 |
| 5,637,787 A | 6/1997 | Fukushima et al. | 73/23.35 |
| 5,689,073 A * | 11/1997 | DaPrato et al. | |
| 5,691,487 A * | 11/1997 | Green et al. | |
| 5,847,291 A * | 12/1998 | Green et al. | |

OTHER PUBLICATIONS

K. Grob, "A Split Injection (Introduction)", pp. 1–9 (and Table of Contents), 1993.

T. Riga, Low Level Analysis of 524.2 Analytes Using a 3000 Purge and Trap and a Varian Direct Split Interface, Tekmar–Dohrmann, Application Note—Spring 94, vol. 4.7.

(List continued on next page.)

Primary Examiner—Jan Ludlow
(74) Attorney, Agent, or Firm—Kirkpatrick & Lockhart LLP

(57) ABSTRACT

A system for concentrating a volatile organic compound (VOC) sample uses in one embodiment a bypass line and a valve coupled thereto to regulate an amount of carrier gas flowing through a carrier gas line. A flow splitter fluidly couples the bypass line to the carrier gas line, and connects to the output of a cryofocuser. The valve opens at the onset of transferring the VOC sample from a concentrator trap such as a sorbent trap to the cryofocuser, thereby resulting in an increased amount of carrier gas flow between the concentrator trap and the cryofocuser for more efficient desorbing of the concentrator trap. The valve is closed when the focused VOC sample is flushed out of the cryofocuser for delivery to a gas chromatograph, preferably delivering the entire VOC sample to the GC.

11 Claims, 3 Drawing Sheets

OTHER PUBLICATIONS

A. Williams, "The Analysis of 524.2 Compounds Utilizing a Split Inlet", Tekmar–Dohrmann, Application Note—Winter 94, vol. 4.2.

W. McClenny et al., "Analysis of VOCs in Ambient Air Using Multisorbent Packings for VOC Accumulation and Sample Drying", Journal of the Air & Waste Management Association, vol. 45, 10/95.

K. Oliver et al., "Technique for Monitoring Toxic VOCs in Air: Sorbent Preconcentration, Closed–Cycle Cooler Cryofocusing, and GC/MS Analysis", Environmental Science & Technology, vol. 30, No. 6, 1986, pp. 1939–1945.

Compendium of Methods for the Determination of Toxic Organic Compounds in Ambient Air, Second Edition, "Compendium Method TO–15—Determination of Volatile Organic Compounds (VOCs) in Air Collected in Specially–Prepared Canisters and Analyzed by Gas Chromatography/Mass Spectrometry (GC/MS)", U.S. Environmental Protection Agency, EPA/625/R–96/010b, 1/97, pp. 15-1–15-63.

Compendium of Methods for the Determination of Toxic Organic Compounds in Ambient Air, Second Edition, "Compendium Method TO–17—Determination of Volatile Organic Compounds in Ambient Air Using Active Sampling Onto Sorbent Tubes", U.S. Environmental Protection Agency, EPA/625/R–96/010b, 1/97, pp. 17-1–17-50.

* cited by examiner

METHOD AND APPARATUS FOR CONCENTRATING A VOC SAMPLE

CROSS REFERENCE TO RELATED APPLICATIONS

This application relates to the following U.S. patent applications, all assigned to the same assignee as the present application and herein incorporated by reference: Ser. No. 08/803,018, "Air Sampler With Trap", which is a continuation of Ser. No. 08/556,620, filed Nov. 13, 1995 now abandoned; Ser. No. 08/556,666. "Coupling of Air Samples to a Sampler", filed Nov. 13, 1995 U.S. Pat. No. 5,691,487, issued Nov. 25, 1997; and Ser. No. 08/556,661, "Verification Circuit for a Fluid Handling Device", filed Nov. 13, 1995 U.S. Pat. No. 5,689,073, issued Nov. 18, 1997.

BACKGROUND OF THE INVENTION

The present invention relates generally to laboratory instruments which concentrate a volatile organic compound ("VOC") sample obtained from a specimen of air, liquid, or soil to prepare such VOC sample for delivery to an analytical instrument such as a gas chromatograph ("GC"). During subsequent analysis, one or more detectors in the GC detects individual analytes from the VOC sample as the analytes sequentially exit the GC column. Such laboratory instruments are generally referred to as sample concentrators. The invention also relates to cryofocusing traps, sometimes referred to as cryofocusers, which can be used together with or as part of a sample concentrator and normally installed at the injection port of the GC for additional concentration ("focusing") of the VOC sample. The invention further has application to laboratory instruments known as autosamplers, which can include a sample concentrator or work in cooperation with one, and which have the capability to sample multiple specimens in an automated sequence.

The invention will be described primarily in connection with an air sample concentrator, but it can also be used with a liquid sample concentrator or a soil sample concentrator. In a liquid sample concentrator (see, e.g., EPA Method 502.2, rev. 2.0 (1989), or EPA Method 524.2, rev. 3.0 (1989), both incorporated herein by reference), the VOC sample is extracted ("purged") from a sample matrix by bubbling an inert purge gas through an aqueous specimen. During this "purge" mode, the inert purge gas, on its way to a vent, passes through a sorbent trap where the VOC sample is retained. Carrier gas during this mode flows through a carrier gas line uncoupled to the sorbent trap. In a subsequent "desorb" mode, the carrier gas line is coupled to the sorbent trap, now at an elevated temperature, and the VOCs are swept out of the sorbent trap to the GC. A soil sample concentrator has a purge and desorb mode like the liquid sample concentrator, except that during the purge mode the purge gas typically bubbles through a mixture of the soil specimen and a liquid such as water.

As used herein, the term "concentrator trap" refers to a device having an "adsorbing state" where VOCs collect or accumulate in the device, and a "desorbing state" where the collected VOCs are released from the device. A sorbent trap comprising a tube filled with one or more layers of sorbent materials is one type of concentrator trap. A glass bead trap comprising a tube packed with glass beads, and temperature controllable to suitably low temperatures, is another type of concentrator trap. "Cryofocuser" as used herein refers to a temperature controlled flow path capable of concentrating a VOC sample delivered to it and releasing the concentrated sample for delivery to a GC or other suitable analytical instrument. Although cryogenic temperatures (less than ambient room temperature, and usually less than about −100° C.) and cryogenic cooling fluids (e.g. liquid nitrogen) are ordinarily used with cryofocusers, they may not always be required in view of unique testing circumstances or future design improvements. Cryofocusers tend to have a smaller internal flow path volume than concentrator traps, with typical volumes for a cryofocuser being about 0.01 to 1 cubic centimeters (cc) and typical volumes for a concentrator trap being about 3 to 30 cc.

Ordinarily, where a cryofocuser is used with a sample concentrator, the cryofocuser is fluidly coupled in series with a carrier gas line, and with the concentrator trap during the desorb mode of the sample concentrator. Afterwards, with the concentrator trap fluidly decoupled from the carrier gas line, carrier gas carries the focused VOC sample from the cryofocuser, which has been rapidly heated, to the GC. At all relevant times, a substantially constant flow rate of carrier gas flows through the carrier gas line to the GC for proper operation of the GC column and detector(s). A drawback associated with such arrangement is that the optimum flow rate for the GC is not necessarily the optimum flow rate for desorbing the analytes from the concentrator trap. Even where a split injection arrangement is used at the injection port of the GC, causing only a portion of the carrier gas flowing through the carrier gas line to flow through the GC, a proportional amount of the VOC sample is discarded and not available for analysis.

Improvements to sample concentrator performance are desired to enable users such as pharmaceutical or environmental testing laboratories to extend the detection limits of current technology and to increase efficiency.

BRIEF SUMMARY OF THE INVENTION

According to one preferred embodiment, a sample concentrator has a carrier gas line, a concentrator trap, a multiple port valve, and a bypass valve. The carrier gas line as a proximal end fluidly coupleable to a source of carrier gas, and a distal end fluidly coupleable to an analytical instrument. The multiple port valve couples to the carrier gas line and to the concentrator trap, and has at least one state fluidly decoupling the carrier gas line from the concentrator trap and at least another state fluidly coupling the carrier gas line to the concentrator trap. The bypass valve fluidly couples to the carrier gas line to permit fluid flow away from the carrier gas line as a function of the state of the bypass valve. A controller is also provided, which directs operation of the multiple port valve and the bypass valve.

According to another preferred embodiment, a system for concentrating a VOC sample for delivery to an analytical instrument includes a flow splitter, a cryofocuser, a bypass line, and a valve. The cryofocuser has an inlet to receive the VOC sample and an outlet fluidly coupleable to the analytical instrument through the flow splitter. The flow splitter also fluidly couples to the bypass line, and the valve regulates gas flow through the bypass line.

A preferred method is disclosed for concentrating a VOC sample before delivery to an analytical instrument. The method includes loading a concentrator trap with the VOC sample, and transferring such sample to a cryofocuser with carrier gas flowing at a first flow rate. The VOC sample is subsequently released from the cryofocuser with carrier gas flowing at a second flow rate. Preferably, the first flow rate is greater than the second flow rate. During the transferring and releasing steps, the flow rate of carrier gas through the analytical instrument preferably remains substantially constant at or below the lesser of the first and second flow rate.

Another preferred method for focusing a VOC sample is disclosed, the method including providing a carrier gas flow through a cryofocuser, carrying the VOC sample to the cryofocuser at a first carrier gas flow rate, and releasing the VOC sample from the cryofocuser for delivery to an analytical instrument at a second carrier gas flow rate.

For convenience, items in the figures having the same reference symbol are the same or serve the same or a similar function.

DETAILED DESCRIPTION OF THE PREFERRED EMBODIMENTS

Figure 1:
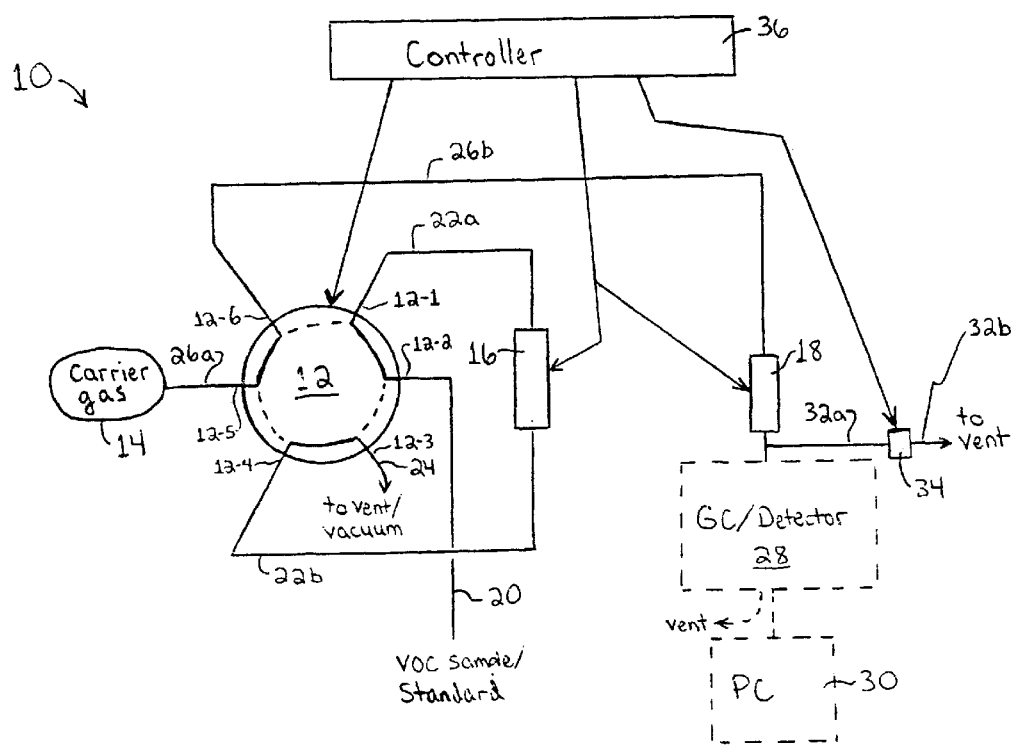
FIG. 1 shows a system for concentrating a VOC sample according to one aspect of the invention.

FIG. 1 shows major components of a system 10 for concentrating a VOC sample. A multiple port valve 12 directs gas flow between a (user-supplied) specimen whose VOC content is to be analyzed, a source of (user-supplied) carrier gas 14, a temperature-controlled concentrator trap 16, and a temperature-controlled cryofocuser 18. Valve 12 is preferably a 6-port rotary valve of conventional design, but it can have a different number of ports and can comprise multiple individual rotary or nonrotary valves arranged to carry out the necessary flow directing functions. Valve 12 has a first state in which the following adjacent ports are fluidly coupled as shown by the solid connections in FIG. 1: ports 12–1 and 12–2, ports 12–3 and 12–4, and ports 12–5 and 12–6. Pneumatic, solenoid, or other suitable actuation rotates an inner block to bring valve 12 into a second state in which the following ports as shown by the dashed connections in FIG. 1 are fluidly coupled: ports 12–2 and 12–3, ports 12–4 and 12–5, and ports 12–6 and 12–1.

In the first state of valve 12, a sample line 20 carries the VOC sample to concentrator trap 16 via trap lines 22a,22b, and on to a vent or vacuum via a line 24. Where system 10 is a liquid or soil sample concentrator, the specimen is sparged in a sparge vessel, vial, or other suitable container with purge gas flowing (typically) for 11 minutes at 40 ml/min. and pressurized relative to the vent at line 24; such process is referred to as a "purge" mode. Where system 10 is a whole air sampler, a measured mass of the air specimen, pressurized relative to the vent, is allowed to flow through line 20 and trap 16; such process is referred to as a "sample transfer" mode. System 10 can alternately comprise a sample tube desorber, where purge gas flushes VOCs out of a tube containing sorbent materials exposed to an air sample in a previous procedure. In any event concentrator trap 16 is held at a sufficiently low temperature to adsorb the VOC sample sent through line 20. During this purge or sample transfer mode, carrier gas flows through a carrier gas line which includes individual lines 26a,26b, through cryofocuser 18, and on to a gas chromatograph/detector 28. Preferably, a computer 30 controls the GC oven temperature and analyzes the output from the GC detector to calculate and display the levels of individual analytes in the VOC sample. Alternately, the control function can be provided in the GC unit 28. With valve 12 in the first state, the carrier gas line is fluidly decoupled from the concentrator trap 16.

The carrier gas source 14 is preferably a pressure-regulated tank or other source of inert gas. The flow rate of carrier gas through the carrier gas line is ordinarily controlled by a pressure regulator internal or external to the GC/detector unit 28 and is dictated by the details of such unit 28: the length and diameter of the GC column, the type of detector used, and whether a split injection technique is used. For a capillary GC column with a mass selective detector (MSD), the carrier gas flow rate is typically about 1 to 5 ml/min at pressures of about 4 to 40 psig.

The embodiment of FIG. 1 however includes a bypass line comprising lines 32a,32b, coupled to the carrier gas line between cryofocuser 18 and the analytical instrument. A valve 34 regulates the amount of carrier gas flow diverted through the bypass line. In the just-described purge or sample transfer mode, valve 34 is preferably closed so that all of the carrier gas flow through the carrier gas line reaches the GC. When valve 34 opens, as will be described below, the carrier gas source 14, which is pressure regulated but preferably not flow regulated, begins supplying an incremental amount of additional carrier gas flow through lines 26a,26b. The incremental carrier gas flow preferably corresponds to the flow through the bypass line, so that the flow of carrier gas through the analytical instrument remains substantially constant thereby avoiding disruption of the analysis. In the second state of valve 12, concentrator trap 16, having been heated to an elevated temperature to release or desorb the previously adsorbed VOC analytes, is coupled to the carrier gas line so that the VOC sample can be transferred to the cryofocuser 18. This process is referred to as a "trap desorb" mode. During at least a portion of this mode and preferably during the entire mode, valve 34 is open and the flow in the bypass line is controlled to increase the carrier gas flow rate through concentrator trap 16 and cryofocuser 18, to a level that will more efficiently and completely remove the VOC sample from the trap 16. The increased flow ensures that even analytes that have migrated deep within trap 16 will be effectively removed, for improved recovery of analytes from the concentrator trap, and resulting improvement in sensitivity and reproducability. Circumstances may also exist where the carrier gas flow rate needs to be decreased during the trap desorb mode for efficient desorbing of trap 16. In such instance valve 34 would be closed during the trap desorb mode.

System 10 also preferably includes a controller 36 which controls actuation of valves 12 and 34, and which controls the temperature of trap 16 and cryofocuser 18 through heating elements such as resistive heaters, cooling elements such as liquid coolants or fans, and temperature sensors such as thermocouples. Controller 36 is of conventional design, and can be resident in a sample concentrator or autosampler base unit, can be installed in computer 30, or a combination thereof. Examples of microprocessor-based controllers are those available with the Model 3000 Purge and Trap Concentrator and the Autocan Air Sampler both sold by Tekmar Co., Cincinnati, Ohio. Such controllers can work in cooperation with computer-based software such as Teklink brand software also available from Tekmar Co.

Figure 2:
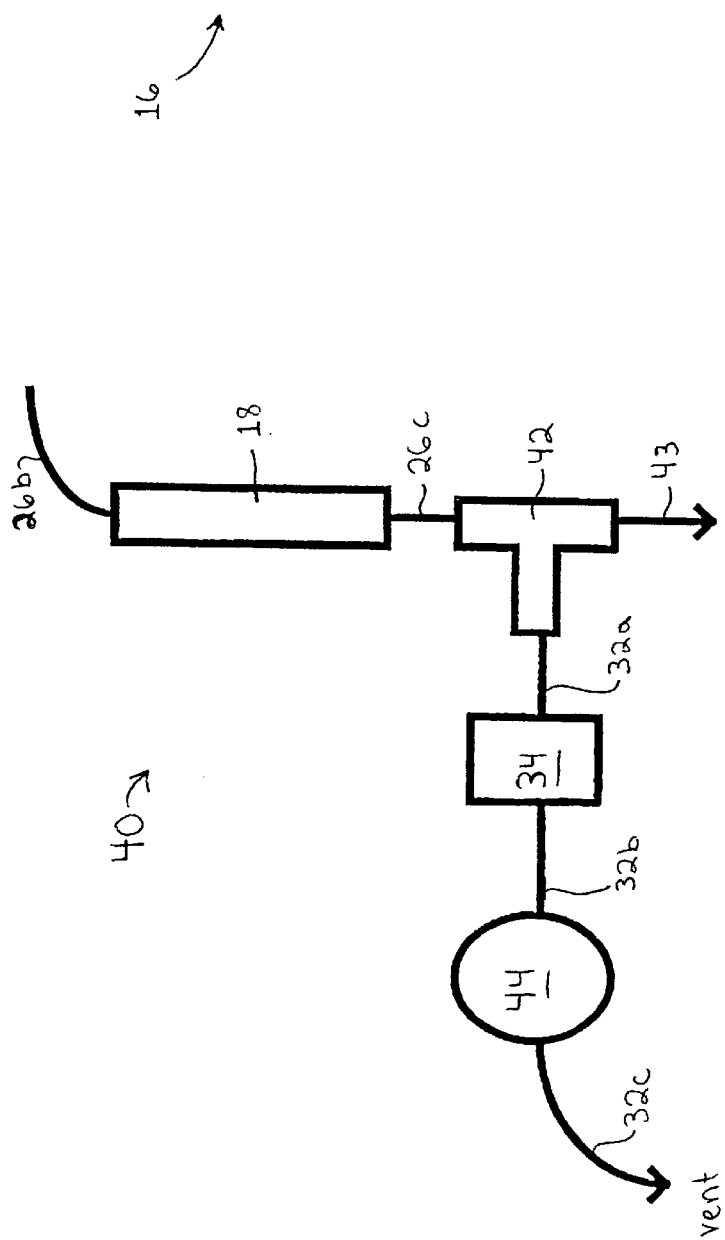
FIG. 2 depicts a preferred flow path connection of a cryofocuser useable in the system of FIG. 1.

In FIG. 2 a preferred cryofocusing system 40 useable in the concentrating system 10 of FIG. 1 is shown. The pneumatic line 26b is shown connected to an inlet of cryofocuser 18, and a line 26c connects the cryofocuser 18 outlet to a T-connector 42 which can operate as a carrier gas flow splitter. A line 43, connected to another port of T-connector 42, is available for connection to the injection port of the GC. If valve 34 is at least partially open, T-connector 42 operates as a flow splitter, dividing carrier gas flow in lines 26b,26c into a first portion sent to the GC by line 43 and a second portion sent to vent by lines 32a–c. If valve 34 is closed, T-connector 42 simply directs all the carrier gas flow in the carrier gas line to the GC by line 43. As mentioned above, the state of valve 34 does not substantially affect the flow rate of carrier gas to the GC (in line 43), since the flow through the GC is controlled by the GC configuration as discussed above. Instead, the opening of bypass valve 34 causes additional carrier gas flow to be drawn from the carrier gas source through the carrier gas line. Preferably a flow control device 44 such as a conventional flow controller, crimped tube, needle valve, or other restrictive device is connected in series with valve 34 to permit adjustment of the incremental carrier gas flow such that the total flow (incremental flow plus flow to the GC) is optimized for desorbing analytes from an upstream trap such as concentrator trap 16. By coupling the flow splitter and bypass valve as shown, different operating modes are permitted which allow both the GC and the desorption of the concentrator trap to be operated at optimum flow rates. The cryofocuser 18 can be of conventional design, for example the Cryofocusing Module (part no. 14-6520-600) is available from Tekmar Co. This Cryofocusing Module comprises a length of fused silica tubing surrounded by a liquid coolant line 18a (see FIG. 3) and by a resistive heater such that the silica tubing can be controlled to temperatures between about −190° C. and +300° C. and can be rapidly heated at a rate of about 550 to 600° C./min. Lines 26b,43, and T-connector 42 are preferably heated to a constant temperature such as 100° C. to prevent adsorption or other loss of analytes. Flow control device 44 is preferably a needle valve of conventional design, e.g. Tekmar Co. part no. 14-5778-050 and manufactured by Valco Instruments Co.

Figure 3:
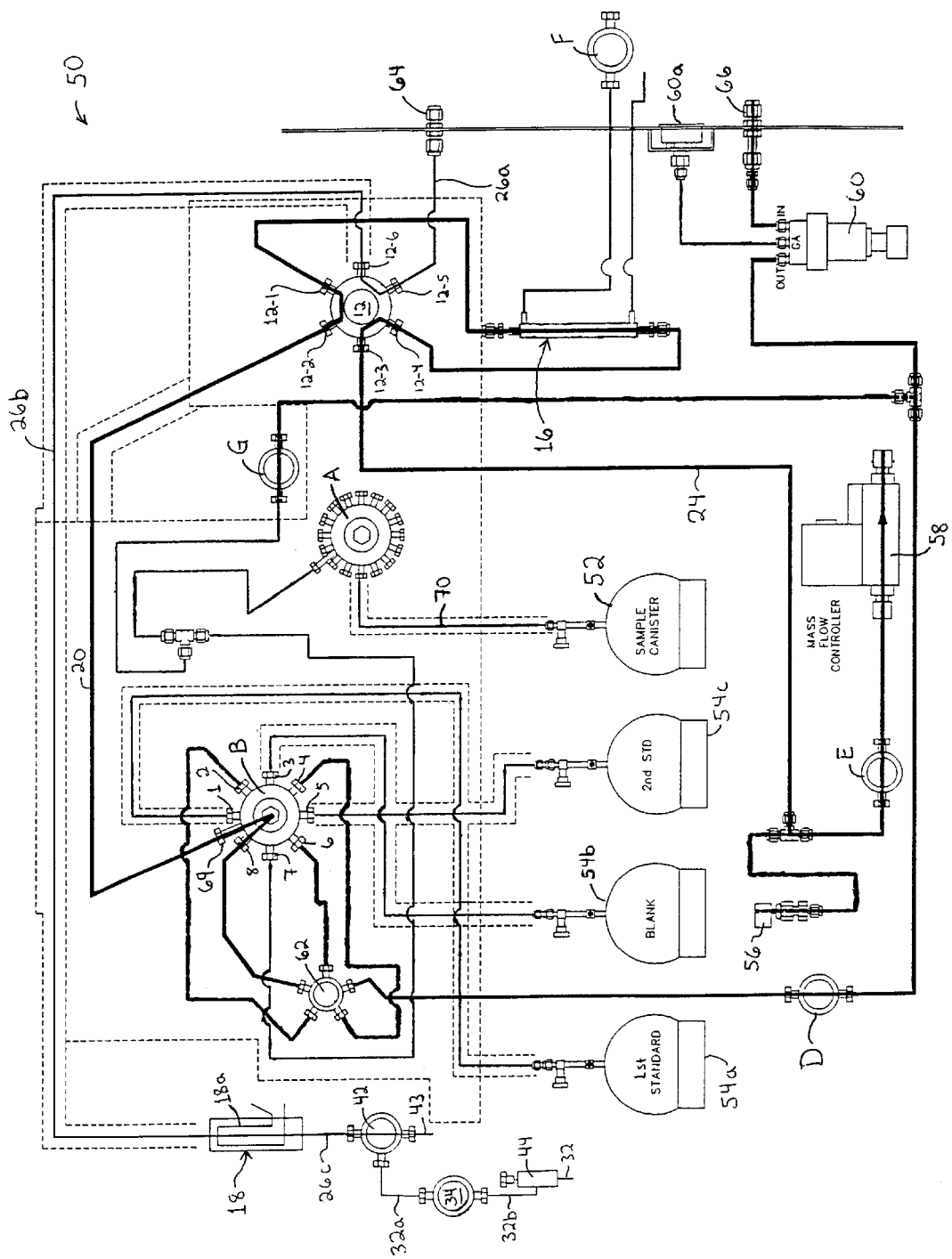
FIG. 3 shows an ambient air autosampler and concentrator apparatus with a cryofocuser according to another aspect of the invention.

FIG. 3 shows a preferred embodiment of an ambient or whole air autosampler 50 according to another aspect of the invention. In FIG. 3, pneumatic lines or connections are shown in solid lines, while broken lines generally indicate heated zones such as ovens for housing one or more valves or heated jackets surrounding pneumatic lines. The heated zones are preferably controlled to a constant temperature such as 200° C.

Many of the components discussed in connection with FIGS. 1 and 2, or like components, are also present in FIG. 3, as shown. New items appearing in FIG. 3 include selection valves A and B, on/off solenoid valves D,E,F,G, a pressure sensor 56, a mass flow controller 58, a pressure regulator 60 and associated pressure gauge 60a, a 5-port connector 62, and various T-connectors and fittings as shown. User-supplied reference standard canisters 54a–c and one of 16 sample canisters 52 containing whole air samples to be tested are also apparent. Other known sample containers such as Tedlar brand bags can be used in place of the SUMMA-type canisters shown.

Not shown is user-supplied carrier gas for connection to a fitting 64. Such carrier gas can be any pure inert gas and commonly is ultrapure helium. Also not shown is user-supplied coolant such as liquid nitrogen for injection through valve F into the cooling jacket shown for concentrator trap 16. Within autosampler 50 trap 16 preferably comprises a multi-layer bed of graphitized carbon-based sorbents (see FIG. 4). Such multi-layer bed permits ambient room temperature adsorption of the VOC sample during the sample transfer mode, and eliminates any need for a separate condensation-type moisture removal device. Use of the cooling jacket and user-supplied coolant results in more rapid cooling, stable temperature control, and gives the user the option to control trap 16 to subambient temperatures if desired. The cooling jacket design is substantially the same as that of the Aerotrap 6000 Sampler sold by Tekmar Co. Alternately, the cooling jacket and liquid coolant can be eliminated and replaced with a conventional air blower or fan for simplicity. User-supplied liquid coolant is also supplied to liquid coolant line 18a and a dedicated solenoid valve (not shown) regulates flow of the coolant for temperature control of cryofocuser 18. Also not shown in FIG. 3 is user-supplied purge gas, referred to also as sweep gas, connected to a fitting 66. Purge gas is an inert gas like the carrier gas but typically controlled to a higher flow rate. Finally, a vent or user-supplied vacuum pump is preferably provided at the output of mass flow controller 58.

Operation of the autosampler 50 will be described in connection with the table below which lists various modes of operation of the autosampler and the states of some of the valves for such modes. For selection valve B, the number listed corresponds to the port fluidly coupled to its output port 69 through a rotatable inner block. For valve 12, "1" refers to its first state discussed above and shown in FIG.3, and "2" refers to its second state discussed above. For solenoid valves D–G, and for valve 34, "1" indicates the valve is on, allowing gas flow, and "0" indicates the valve is off, inhibiting gas flow. Combination entries mean that any one of the indicated states are permissible.

| MODE OF OPERATION | B | 12 | D | E | F | G | 34 |
|---|---|---|---|---|---|---|---|
| Standby | 2/4/6/8 | 1 | 1 | 1 | 0 | 0 | 0 |
| System Leak Check | 2/4/6/8 | 1 | 0 | 0 | 0 | 0 | 0 |
| Trap Cool/Cryofocus Cool | 2/4/6/8 | 1 | 0 | 0 | 1 | 0 | 0 |
| 1st Standard Transfer | 1 | 1 | 0 | 1 | 1 | 0 | 0 |
| Blank Transfer | 3 | 1 | 0 | 1 | 1 | 0 | 0 |
| 2nd Standard Transfer | 5 | 1 | 0 | 1 | 1 | 0 | 0 |
| Sample Transfer | 7 | 1 | 0 | 1 | 1 | 0 | 0 |
| Drypurge | 2/4/6/8 | 1 | 1 | 1 | 1 | 0 | 0 |
| Trap Desorb Ready | 2/4/6/8 | 1 | 0 | 0 | 1 | 0 | 0 |
| Trap Desorb | 2/4/6/8 | 2 | 1 | 1 | 0 | 0 | 1 |
| Next Sample Pressure Check | 7 | 1 | 0 | 0 | 0 | 0 | 0 |
| Inject/Bake | 2/4/6/8 | 1 | 1 | 1 | 0 | 0 | 0 |
| Backflush | 2/4/6/8 | 1 | 0 | 0 | 0 | 1 | 0 |
| Sample Leak Check | 7 | 1 | 0 | 0 | 0 | 0 | 0 |
| Leak Check 1st Standard | 1 | 1 | 0 | 0 | 0 | 0 | 0 |
| Leak Check "Blank" | 3 | 1 | 0 | 0 | 0 | 0 | 0 |
| Leak Check 2nd Standard | 5 | 1 | 0 | 0 | 0 | 0 | 0 |

In "Standby" mode, autosampler 50 is essentially idle. No samples are taken from sample canisters 52 or from standard canisters 54a–c. Purge gas flows through trap 16 via fitting 66, valve D, selection valve B, valve 12, valve E, and flow controller 58. Trap 16 and cryofocuser 18 are neither cooled nor heated. This "Standby" mode is identical to other modes of autosampler 50 not shown in the table, such as a "GC Synch" mode where the controller of autosampler 50 (see, e.g., FIG. 1) waits for a synchronization signal from the GC 28 to advance to the next mode.

In "System Leak Check" mode, valves D and G are shut off and a vacuum is created in the lines, valves, and fittings between those valves D and G and mass flow controller 58, which is connected to a vacuum pump. Valve E is then also shut off, and the autosampler 50 controller monitors the output of pressure sensor 56. A leak condition is indicated if the measured pressure rises unacceptably over time.

In "Trap Cool/Cryofocus Cool" mode, liquid coolant is routed through valve F to cool concentrator trap 16. Liquid coolant is also routed through liquid coolant line 18a to cool cryofocuser 18.

In "1st Standard Transfer" mode, valves B and 12 cooperate to allow flow of gas from the 1st standard canister 54a through trap 16. The autosampler controller monitors mass flow controller 58 so that a programmed mass of the standard is sent through trap 16. Preferably, all pneumatic tubing connected between the cryofocuser 18 and each of the standard canisters 54a–c and the sample canisters 52 comprise highly inert yet flexible SilcoSteel® brand tubing available from Restek Corp. Such pneumatic tubing includes a terminal portion of line 26b, referred to in the art as a "transfer line", operable to transfer the VOC sample from the autosampler or sample concentrator unit to the GC. The terminus of the transfer line can be coupled directly to the GC injection port or, as shown in FIGS. 1, 2, and 3, coupled through a cryofocuser. The transfer line can alternately comprise a conventional fused silica line or capillary. Lines not connected between cryofocuser 18 and each of canisters 54a–c and 52 can comprise standard nickel or steel tubing for reduced cost. "Blank Transfer" mode is similar to "1st Standard Transfer" mode, except that gas from the blank canister 54b is sampled. In the optional "2nd Standard Transfer" mode gas from canister 54c is sampled.

In "Sample Transfer" mode, a programmed mass (specimen) of gas from one of the sample canisters 52 as directed by selection valve A is sent through trap 16 where VOCs from such specimen are collected. Trap 16 is controlled to a sufficiently low temperature to adsorb the received VOCs. The remaining gas specimen exits the mass flow controller 58 to vent.

In "Drypurge" mode, purge gas is directed through the trap 16, which is still maintained at a low temperature to retain the VOCs. However, the purge gas carries residual moisture which may be resident in trap 16 and which originated from the air sample to vent.

In "Trap Desorb Ready" mode, autosampler 50 is essentially idle as it waits for a suitable signal from the GC indicating that any previous sample has been completely analyzer. Purge gas flow to trap 16 is shut off, and trap 16 can remain at its low temperature.

In "Trap Desorb" mode, valve 12 changes state to backflush trap 16 with carrier gas flow. Trap 16 is now controlled to a high temperature sufficient to desorb the analytes from the trap. Also, valve 34 opens to permit additional carrier gas flow through bypass lines 32a,32b and thus increase the backflush flow through trap 16, resulting in more efficient desorption. Cryofocuser 18, held at a low temperature, collects and focuses the VOC sample desorbed from trap 16.

In "Next Sample Pressure Check" mode, valve 12 returns to its first state, selection valve B rotates to position 7, selection valve A advances to the next gas sample to be analyzed, and valves D,G,and E are closed so that pressure sensor 56 can measure the pressure in the selected sample canister 52, thus verifying sample integrity.

In "Inject/Bake" mode, the cryofocuser is rapidly heated to release the VOC sample in a tight plug to the GC. Trap 16 can be heated to its bake temperature (e.g. 350° C.) during this mode.

In "Backflush" mode, purge gas backflushes selection valve A and the pneumatic lines 70 as valve A is cycled through each port. The sample canisters 52 are of course disconnected from the lines 70 during this mode. "Sample Leak Check" mode is similar to "System Leak Check" mode, except that the sample lines are monitored for a programmed time to detect a leak between the sample canister 52 and valve E. The modes "Leak Check 1st Standard", "Leak Check 'Blank'", and "Leak Check 2nd Standard" are all analogous to "Sample Leak Check" mode.

Figure 4:
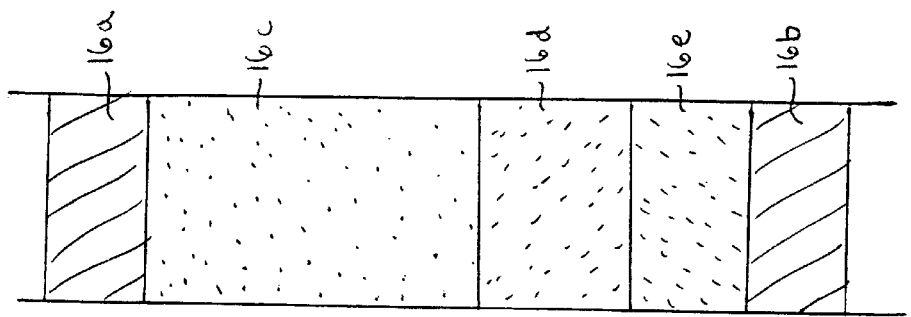
FIG. 4 is a representation of a preferred sorbent trap useable in the apparatus of FIG. 3.

FIG. 4 shows a preferred configuration of concentrator trap 16 for use with the whole air autosampler 50 of FIG. 3. Packed in a tube between glass wool layers 16a,16b are three layers of different graphitized carbon-based sorbents (GCBS): layer 16c having a relatively low affinity to light VOC compounds and preferably comprising Carbopac B material available from Supelco Co.; layer 16d having an intermediate affinity to light VOC compounds and preferably comprising Carboxen 1000 material available from Supelco Co.; and layer 16e having a relatively strong affinity to light VOC compounds and preferably comprising Carboxen 1001 material available from Supelco Co. The tube is connected to the flow lines such that the VOC sample is loaded through layer 16a and backflushed during desorption back out layer 16a. Preferred thicknesses of the layers are: 0.25 inch (6 mm) for layers 16a and 16b; 2.4 inches (61 mm) for layer 16c; 1.4 inches (35 mm) for layer 16d; and 0.24 inches (6 mm) for layer 16e. The disclosed sorbent trap configuration has been found effective to trap VOC compounds of interest at ambient room temperature with hydrophobic GCBS materials that advantageously permit removal of water vapor from the VOC sample without requiring condensation-based moisture removal devices. However, it is recognized that other single or multilayer sorbent traps with GCBS or non-GCBS materials, and glass bead traps, can also be used in the autosampler 50.

Although the present invention has been described with reference to preferred embodiments, workers skilled in the art will recognize that changes can be made in form and detail without departing from the spirit and scope of the invention.

What is claimed is:

1. A sample concentrator, comprising:
   a focusing trap having an inlet and outlet, and being operable between a focusing absorb mode and a focusing desorb mode;
   a focusing trap feed line connected in series to the inlet of the focusing trap;
   an instrument feed line connected in series to the outlet of the focusing trap;
   a bypass line fluidly coupled to the instrument feed line;
   a bypass valve fluidly interposed between the bypass line and a vent, for regulating flow rate through the bypass line;
   a concentrator trap having a concentrator absorb mode and a concentrator desorb mode, the concentrator trap being selectively in fluid communication with the focusing trap through the focusing trap feed line;
   at least one trap controller operably coupled to the focusing trap and the concentrator trap for operating the focusing and concentrator traps between their respective absorb and desorb modes; and
   a valve controller operably coupled to the bypass valve for operating the bypass valve to impede flow through the bypass valve during the focusing desorb mode, the valve controller being further configured to encourage flow through the bypass valve when the concentrator trap is in the concentrator desorb mode and is in fluid communication with the focusing trap.

2. The sample concentrator of claim 1, wherein the focusing trap is a cryofocuser.

3. The sample concentrator of claim 1 wherein the bypass line includes a flow control device coupled to the bypass line for adjusting flow through the bypass line.

4. The sample concentrator of claim 1 wherein bypass line is connected to the instrument feed line by a T connector.

5. The sample concentrator of claim 1 wherein the instrument feed line is connected to a gas chromatograph.

6. The sample concentrator of claim 2 wherein the inlet of the cryofocuser is selectively coupled to a sample source via a multiple port valve to selectively couple and decouple the sample source to the cryofocuser.

7. The sample concentrator of claim 6 wherein the sample source includes the concentrator trap, and wherein the sample source is decoupled from the cryofocuser in the concentrator absorb mode and coupled to the cryofocuser in the concentrator desorb mode.

8. The sample concentrator of claim 6, further comprising:
   a sample selection valve having an outlet fluidly coupled to the multiple port valve and a plurality of inlets fluidly coupleable respectively to a plurality of specimens to be tested for VOC content.

9. The sample concentrator of claim 1, wherein the focusing trap is in the focusing absorb mode when in fluid communication with the concentrator trap in the concentrator desorb mode.

10. The sample concentrator of claim 9, further comprising a source of flow in fluid communication with an inlet of the concentrator trap, the source of flow being configured to provide an increased fluid flow through the concentrator trap when the concentrator trap is in the concentrator desorb mode.

11. The sample concentrator of claim 1, further comprising a source of flow adapted to provide an increased fluid flow through the concentrator trap when the concentrator trap is in the concentrator desorb mode.

* * * * *